United States Patent [19]
Potter

[11] Patent Number: 4,534,355
[45] Date of Patent: Aug. 13, 1985

[54] ELECTROCHEMICAL SENSOR EMPLOYING A GAS-PERMEABLE HYDROPHILIC POLYURETHANE MEMBRANE

[75] Inventor: William D. Potter, Hertfordshire, England

[73] Assignee: Smith and Nephew Associated Companies Inc., England

[21] Appl. No.: 364,864

[22] PCT Filed: Oct. 13, 1981

[86] PCT No.: PCT/GB81/00223
§ 371 Date: Mar. 26, 1982
§ 102(e) Date: Mar. 26, 1982

[87] PCT Pub. No.: WO82/01306
PCT Pub. Date: Apr. 29, 1982

[30] Foreign Application Priority Data
Oct. 15, 1980 [GB] United Kingdom ............... 8033313

[51] Int. Cl.³ .............................................. A61B 5/00
[52] U.S. Cl. .................................. 128/635; 204/403; 204/415; 204/431
[58] Field of Search ............... 128/635, 632; 204/403, 204/415, 433, 431; 524/591

[56] References Cited
U.S. PATENT DOCUMENTS

| | | | |
|---|---|---|---|
| 4,041,933 | 8/1977 | Reichenberger | 128/635 |
| 4,061,618 | 12/1977 | Stanley et al. | 524/591 |
| 4,273,636 | 6/1981 | Shimeda et al. | 128/635 X |

FOREIGN PATENT DOCUMENTS

| | | | |
|---|---|---|---|
| 15075 | 9/1980 | European Pat. Off. | 128/635 |
| 131414 | 6/1978 | Fed. Rep. of Germany | 204/415 |

Primary Examiner—Lee S. Cohen
Attorney, Agent, or Firm—Jacobs & Jacobs

[57] ABSTRACT

A device for use in determining blood gas which employs a membrane of material permeable to blood gas to be determined characterized in that the membrane is hydrophilic polyurethane is described.

10 Claims, 9 Drawing Figures

ELECTROCHEMICAL SENSOR EMPLOYING A GAS-PERMEABLE HYDROPHILIC POLYURETHANE MEMBRANE

FIELD OF THE INVENTION

The present invention is concerned with certain medical devices which employ hydrophilic polyurethanes and is also concerned with certain hydrophilic polyurethanes suitable for such a purpose. More specifically this invention is concerned with medical devices for determining blood gas which devices employ a membrane of hydrophilic polyurethanes and is also concerned with certain hydrophilic polyurethanes suitable for use in such devices.

DESCRIPTION OF THE PRIOR ART

Medical devices used to determine blood gas levels normally employ a membrane which allows the passage of a specie involved in the determination while preventing the passage of materials such as proteins that could disadvantageously effect the operation of the device. Such medical devices are generally those which are employed in contact with the body although some devices are used in conjunction with extracorporeal circulation of blood or blood samples otherwise removed from the body. Whereas this invention is concerned with medical devices which can be used in either or both these modes it is especially concerned with medical devices suitable for use in contact with the body (even if the devices are also suitable for use away from the body). The body contact medical device will normally be one adapted to operate in contact with a body fluid such as blood, perspiration or a fluid exuded from a lesion. Whereas the devices of this invention offer considerable advantages when adapted to contact a body fluid such as perspiration or exudate on the exterior surface of the body, the advantages are most profound in medical devices used in direct contact with blood present in the circulation of the patient.

Devices for determining blood gases or electrolytes are normally either electrochemical sensors or collection devices. Electrochemical sensors are devices which in the presence of the relevant specie produce an electrical change as a result of a chemical change (which includes change of the concentration of a species). Collection devices serve to transport the gas to another place for determination. The medical devices with which this invention is particularly concerned are electrochemical sensors.

Electrochemical sensors which may be used for the determination of blood gases are described in, for example, British Patent Specifications Nos. 1265505, 1325873, 1503908, 2005418 and 2055476, U.S. Pat. Nos. 3,088,905 and 3,912,614, European Patent Specifications Nos. 0015075 and 0027385 and Med. and Biol. Eng. Comput., 1978, 16, 599-600. The publications describe blood gas detectors requiring the presence of membranes and a number of useful or potentially useful membrane materials are described. Some of the publications disclose the advantages of using hydrophilic materials such as polyHEMA but none suggest that hydrophilic polyurethanes may be employed in blood gas detectors.

Hydrophilic polyurethanes have been previously described in, for example, U.K. Patent Specification No. 1551620, U.S. Pat. Nos. 3,975,350, 3,822,238, 4,156,067 and C. T. Chen. et. al., J. Appl. Polymer Science Vol. 16, p. 2105-2114 (1972). However none of these documents suggest the use of hydrophilic polyurethanes in devices for determining the concentrations of blood gases.

SUMMARY OF THE INVENTION

It has now been found that hydrophilic polyurethanes membranes can be employed in devices for determining blood gas and that advantages can be found to accrue from use of hydrophilic polyurethane in various medical devices of this invention selected from good binding of the membrane to the mounting, rapid response time, rapid equilibration time, reduction in dependency upon certain electrolytes used within certain types of device and simplification of manufacture.

The present invention provides a medical device for use in determining blood gas which employs a membrane of material permeable to the blood gas to be determined characterised in that the membrane is hydrophilic polyurethane.

The medical device of this invention either may be adapted for use remote from the body, for example in conjunction with an extracorporeal circulation of blood or with an isolated blood sample, or may be adapted for use in contact with the body. The desirable properties imparted by the use of hydrophilic polyurethane is manifest in both classes of device but it is believed that the greatest advantages occur with body contact devices in view, inter alia, of the improved biocompatibility of the medical device employing the hydrophilic polyurethane. Certain medical devices of this invention which benefit most from the use of membranes of hydrophilic polyurethane are those adapted for use in contact with arterial or, more usually, venous blood. The hydrophilic polyurethane employed will be compatible with the body fluid, that is it is stable in the presence of blood or other vital fluid and the tissue is not damaged. The compatibility of the hydrophilic polyurethane membrane with respect to blood is of great advantage for devices contacting arterial or venous blood. Other medical devices which benefit considerably from the use of membranes of hydrophilic polyurethane are those which are adapted for use in contact with the skin.

It is believed that for use in this invention it is desirable that the hydrophilic polyurethane will have a water content in the hydrated state of from 5 to 50% water, more aptly 10 to 40% water, suitably 15 to 35% water and preferably 20 to 30% water (% water content calculated on weight of water in polymer having been immersed in water at 20° C.; % water content can be determined by the obvious expedient of weighing a dry sample, allowing it to equilibrate in water and reweighing it after wiping off external moisture). Thus apt devices of this invention employ hydrophilic polyurethanes which hydrated contain 10 to 40% water, particularly suitable devices of this invention employ hydrophilic polyurethanes which hydrated contain 15 to 35% water and preferred devices of this invention employ hydrophilic polyurethanes which hydrated contain 20 to 30% water.

The hydrophilic polyurethane membrane of the devices of this invention will normally be in contact with the body when the device is in use (for example by contact with blood or skin) so that the device is characterised in that it is coated on a body contacting surface with hydrophilic polyurethane. This coating (that is the membrane) will normally be from 3 to 50 microns thick and generally be from 10 to 25 microns thick, for example about 10, 20 or 25 microns thick. Such thickness of hydrophilic polyurethane can result in very favorable response and equilibration times. However, if desired, thicker membranes can be employed, for example 50 to 100 microns but, in general, these are envisaged as being less desirable than the thinner membranes hereinbefore set forth.

It is envisaged that the hydrophilic polyurethane will be present in the medical device until use as the unhydrated form but that in use it becomes hydrated by taking up water from its new environment or else by wetting just prior to use. The aforementioned thickness of the hydrophilic polyurethane membrane refer to the unhydrated form.

It has now also been found that coatings of the desired thickness can be readily obtained on the devices of this invention by employing hydrophilic polyurethanes which are linear (that is substantially free of crosslinking and thereby soluble in organic solvents such as methylene chloride or other solvent hereinafter indicated). Thus devices of this invention will most suitably employ a hydrophilic polyurethane which is linear.

The medical devices of this invention may be adapted to determine either oxygen or carbon dioxide but certain favored medical devices are adapted to determine both oxygen and carbon dioxide simultaneously. Medical electrochemical sensors of this sort are frequently referred to as electrodes. Favoured electrodes suitable for determining oxygen and carbon dioxide which benefit from the use of hydrophilic polyurethanes in the manner of this invention include those of British Patent Specification No. 2005418A (which is incorporated herein by cross reference). Such devices include those which may be used to contact blood (normally venous blood) and those which may be used to contact the skin (when transmission via perspiration may occur). The polystyrene membrane of the known devices may be replaced by a membrane of hydrophilic polyurethane. A coating of hydrophilic polyurethane was applied overthe operating area of electrode per se and over its surroundings, for example over the catheter in which the blood contacting electrode is mounted.

It is a considerable advantage of this invention that a hydrophilic polyurethane membrane is provided that does not peel away from conventional materials used for mounting the electrochemical sensors such as polyvinylchloride or nylon when the membrane hydrates, for example, after being placed in blood. It has now been found that for this property to be best exhibited, hydrophilic polyurethanes with a water content of not more than 50%, more favourably not more than 40%, preferably not more than 35% and most preferably not more than 30% are best suited for use in the devices of this invention. This is especially so when the devices are intended for use in contact with arterial, or more usually, venous blood and are mounted at the distal end of a catheter, for example of PVC, nylon or the like.

It is a considerable advantage of this invention that the hydrophilic polyurethanes allow a rapid response and rapid equilibrium times. For optimisation of such properties the membrane material when hydrated contains not less than 5% water, more aptly not less than 10% water, favorably not less than 15% water and preferably not less than 20% water.

Certain favored devices of this invention comprise an oxygen electrode mounted at the distal end of a catheter for intravenous use which electrode employs a membrane permeable to oxygen characterised in that the membrane is linear hydrophilic polyurethane. Most aptly the linear hydrophilic polyurethane when hydrated contains 10 to 40% water and preferably contains 20 to 30% water.

Other favored devices of this invention comprises a carbon dioxide electrode mounted at the distal end of a catheter for intravenous use which electrode employs a membrane permeable to carbon dioxide characterised in that the membrane is linear hydrophilic polyurethane. Most aptly the linear hydrophilic polyurethane when hydrated contains 10 to 40% water and preferably contains 20 to 30% water.

Yet other favored devices of this invention comprises an electrochemical sensor capable of monitoring oxygen and carbon dioxide mounted at the distal end of a catheter for intravenous use which electrode employs a membrane permeable to oxygen and carbon dioxide characterised in that the membrane is linear hydrophilic polyurethane. Most aptly the linear hydrophilic polyurethane when hydrated contains 10 to 40% water and preferably contains 20 to 30% water.

In blood contact devices such as those adapted to measure carbon dioxide and which employ an internal electrolyte, the use of hydrophilic polyurethane reduces the criticality of having closely controlled concentration and distribution of the electrolyte since electrolyte from the blood can diffuse through the membrane. This useful property is more aptly displayed by polymers which contain not less than 10%, more favourably not less than 15% and preferably not less than 20% of water when hydrated. Generally it is not apt to employ polymers which contain more than 50%, more favourably not more than 40%, most favourably not more than 35% and preferably not more than 30% water when hydrated in such devices.

The membrane of the foregoing devices is normally on the outer surface of the device (that is on a body contacting surface) and it has been found that such membranes can be readily applied by dip coating from a solution of the polymer in a solvent which is normally one in which the catheter is not soluble. The catheters may be of any suitable material such as PVC or nylon. The hydrophilic polyurethane can be used to form a membrane over the catheter as well as over the electrochemical sensor. However for a bilumen catheter in which an access port is employed the membrane may be applied by painting or by dip coating to a level distal to the port.

Preferred hydrophilic polyurethanes for use in this invention are polyether polyurethanes. It is not preferred to employ hydrophilic polyurethanes which are polyester polyurethanes or which have potentially reactive substituents such as hydroxyl or carboxyl groups.

Apt polyether polyurethanes for use in this invention will be random polymers containing units derived from diolic compound and di-isocyanates.

Aptly the ether units in the hydrophilic polyurethane for use in this invention will be notionally derivable from ethylene diol and a propylene or butylene diol; that is they will contain $CH_2CH_2O-$ units and $-CH_2CH_2CH_2O-$, $-CH_2CH(CH_3)O-$ or $-CH_2CH_2CH_2CH_2O-$ units. Most aptly the ether units in the polyurethane will contain $-CH_2CH_2O-$ and $-CH_2CH(CH_3)O-$ or $-(CH_2)_4O-$ mixtures thereof of which poly $-CH_2CH(CH_3)O-$ blocks are preferred. Desirably the mole ratio of poly(ethylene glycol) to poly[(prop or but)ylene glycol] derivable blocks present in the hydrophilic polyurethanes vary between 1:1 to 1:30, more suitably from 1:2 to 1:10 and preferably from 1:2.5 to 1:4. The molecular weights of these blocks is aptly from 600 to 6000 and favourably from 900 to 4000, for example 1000 to 2000.

Most aptly the hydrophilic polyurethane for use in this invention will contain residues of aliphatic diols of up to 10 carbon atoms and more suitably up to 4 carbon atoms (of which ethane diol is preferred) as chain extenders wherein the mole ratio of diol to polyglycol used in the preparation of the polymer is from 3:1 to 1:4, more aptly 5:2 to 1:3 and preferably from 2:1 to 1:2.

The hydrophilic polyurethane will contain sufficient di-isocyanate residues to produce the water contents set forth hereinbefore when the polymer is hydrated.

Most aptly the hydrophilic polyurethane for use in this invention will contain di-isocyanate residues which may be residues of aromatic or aliphatic di-isocyanates such as 4,4'-diphenylmethane di-isocyanate, toluene di-isocyanate, 1,6-hexamethylene di-isocyanate, 4,4'dicyclohexylmethane di-isocyanate or the like. Favoured di-isocyanates for use in the hydrophilic polyurethane of this invention are 4,4'-dicyclohexylmethane di-isocyanate (which is preferred) and 4,4'-diphenylmethyl di-isocyanate.

Less aptly than using aliphatic diol chain extenders, the hydrophilic polyurethane may employ equivalent quantities of aliphatic diamine or aliphatic amineol chain extenders of which ethylene diamine is preferred. Similarly somewhat less aptly than using aliphatic diol chain extenders, the hydrophilic polyurethane may employ an aromatic diamine such as phenylenediamine, benzidine or diaminodiphenylmethane.

Less aptly than using a mixture of poly(ethylene glycol) and poly[(prop or but)ylene glycol] derived blocks, the hydrophilic polyurethane may employ poly(ethyleneglycol) derived blocks alone together with a higher proportion of chain extender and di-isocyanate.

Normally and preferably the hydrophilic polyurethane used in the devices of this invention is essentially a single type of polymer (a product of the polymerisation of the same materials) although blends may be employed to form the hydrophilic polyurethane if desired.

Most aptly the hydrophilic polyurethane employed in this invention is one that if a micron thick will transmit at least 15000 and preferably at least 20000 g/m$^2$/24 hrs/20° C./RH 100-70% (Payne Cup method) and most aptly the hydrophilic polyurethane employed in this invention will have a very high transmission value for oxygen and carbon dioxide of at least 5 and preferably at least 10 ml (STP) cm $\times$ 10$^{10}$/cm$^2$ cmHg·Sec.

The devices of this invention may be prepared by any convenient method of coating surfaces such as dip coating, spraying, painting or the like. In such processes the hydrophilic polyurethane is dissolved in a suitable organic solvent, for example as a 1–10% solution or more aptly as a 2.5–5% solution. Suitable organic solvents include halogenated hydrocarbons such as dichloromethane, alkanols such as methanol or ethanol (optionally containing small amounts of water), ketones such as acetone or methylethylketone or mixtures thereof, for example a mixture of dichloromethane and methanol, for example in a ratio of about 4:1 or a mixture of dichloromethane and ethanol optionally containing about 2% water, for example in a ratio of about 1:1.

Normally and preferably the hydrophilic polyurethane will be applied in the non-hydrated state. The hydrophilic polyurethane may be hydrated thereafter if desired but normally hydration will not be carried out until use or shortly before.

Sensors mounted at the distal end of catheters may be coated by drawing the catheter upward through a solution of the hydrophilic polyurethane and causing or allowing the solvent to evaporate, for example by drying in air at ambient or elevated temperature, for example up to 80° C. Sensors mounted at the distal end of catheters and other forms of electrodes can also be coated by painting the appropriate part with a solution of the hydrophilic polyurethane and then allowing or causing the solvent to evaporate. Membranes formed in such a manner are flexible and firmly bound to the electrode and to other surfaces contacted during the coating such as polyvinyl chloride or nylon mountings or the like even after hydration. Generally a single dipping is sufficient to provide a film of the desired thickness but of desired a second dipping may be used for thicker films.

In less favoured forms of this invention which employ a preformed film of the hydrophilic polyurethane, this may be made by casting small squares of film from solution in a 1:1 mixture of methylene chloride and ethanol containing 2% water onto a silicone release paper. Generally about a 15% solution is employed using a doctor blade with a gap of about 60 microns and drying for about 5 minutes at 70° C. to remove solvent. The resulting film is about 15 to 25 microns thick and is less brittle than dry polyHEMA films. In a much less apt form the hydrophilic polyurethane may be cast onto a 10 to 15 micron thick low density polyethylene film and used in the two component form.

The present invention also provides novel linear hydrophilic polyurethanes which consist essentially of 4,4'dicyclohexylmethyl or 4,4'diphenylmethyl residues and alkylene residues are selected from (a) aliphatic diol residues of up to 10 carbon atoms (b) poly(ethylene glycol) blocks (that is blocks of —CH$_2$CH$_2$O— residues) and (c) poly[(prop or but)ylene glycol] blocks (that is blocks of CH$_2$CH(CH$_3$)O— or CH$_2$CH$_2$CH$_2$CH$_2$O— residues) wherein the mole ratio of (a):(b)+(c) is from 3:1 to 1:4 and the mole ratio of (b):(c) is from 1:2 to 1:30.

Most aptly the hydrophilic polyurethane contains 4,4'dicyclohexylmethane di-isocyanate residues. Most aptly the component (c) is composed of blocks of CH$_2$CH(CH$_3$)O— residues. Most aptly component (a) is ethane diol residues (that is CH$_2$CH$_2$O— residues).

Normally and preferably the novel polyurethane of this invention is adapted to absorb the levels of water set forth hereinbefore. Water absorbencies within these ranges may be obtained by varying the ratio of (a), (b) and (c) within the limits specified hereinbefore.

Most aptly the mole ratio of poly(ethylene glycol) to poly[(prop or but)ylene glycol] derivable blocks present is from 1:2 to 1:10, favourably from 1:2.5 to 1:4 and preferably 1:3.

Highly favored hydrophilic polyurethanes of this invention consist essentially of 4,4' dicyclomethane residues and alkylene residues selected from (a$^1$) —CH$_2$CH$_2$O— residues, (b$^1$) blocks of —CH$_2$CH$_2$O— residues and (c$^1$) blocks of —CH$_2$CH(CH$_3$)O— residues wherein the mole ratio of (a$^1$) (b$^1$)+(c$^1$) is from 2:1 to 1:1 and the mole ratio of (b$^1$):(c$^1$) is from 1:2.5 to 1:4.

An apt mole ratio of $(a^1):(b^1)+(c^1)$ is 1.5:1. An apt mole ratio of $(b^1):(c^1)$ is 1:3.

Particularly apt polymers of this invention comprise polyethylene glycol residues, polypropylene glycol residues, ethane diol residues and 4,4'-dicyclohexylmethane di-isocyanate residues in the mole ratios 1:2.5–3.5:.5–7:9–12; more suitably 1:2.8–3.2:5.5–6.5:9.5–11.5 and most suitably 1:3:6:10.5–11.5.

A preferred polymer of this invention comprises polyethylene glycol 1540 residues, polypropylene glycol 1025 residues, ethane diol residues and dicyclohexylmethane di-isocyanate residues in the mole ratios 1:3:6:10. This preferred polymer of the invention has a water content when hydrated of about 26% when freshly prepared.

The polymers of this invention may be prepared by blending together the reactants (that is the diol, polymeric ethers, di-isocyanate) and optionally water and adding thereto the polymerization catalyst. Generally the polymerization is carried out at a moderately elevated temperature such as 50° to 90° C., which can be maintained by the reactants exotherm and finally cured at a slightly elevated temperature such as 70° to 100° C. The product of this reaction is generally a foam. This material may be used to prepare solutions for coating the medical devices of this invention by dissolving the foam in an appropriate solvent.

The catalyst employed may be any convenient catalyst such as tertiary amine or organo metallic compound such as di-n-butyl-tin dilaurate. Such catalysts will generally be employed in conventional amounts such as 0.05 to 0.5% for example 0.2%.

The di-isocyanate groups and hydroxy groups are present in the reaction mixture in approximately equimolar quantities (so that the final product is substantially free of isocyanate groups or organic hydroxyl groups) but a small amount of water (aptly 0.1 to 0.5%) may be present. Generally a slight molar excess of di-isocyanate over organic hydroxy compound is employed (e.g. 1:1.1).

The polymers are normally room temperature conditioned before use or testing (as is conventional in the polyurethane art). Such conditioning may take 1 to 4 weeks if desired.

The devices of this invention are normally used in sterile form. Sterilization may be achieved in conventional manner, for example by irradiation.

The devices of this invention may also be used for non-medical uses such as monitoring oxygen levels in industrial gas. Thus this invention also porvides an oxygen electrode which requires the presence of a protective membrane which is permeable to oxygen characterised in that the membrane is hydrophilic polyurethane.

The medical devices of this invention may be of conventional design such as those shown in FIGS. 1-9 herein.

DETAILED DESCRIPTION OF THE INVENTION

The hydrophilic polyurethane employed in the devices of FIGS. 1 to 9 is very aptly that of Example 2.

Figure 1:
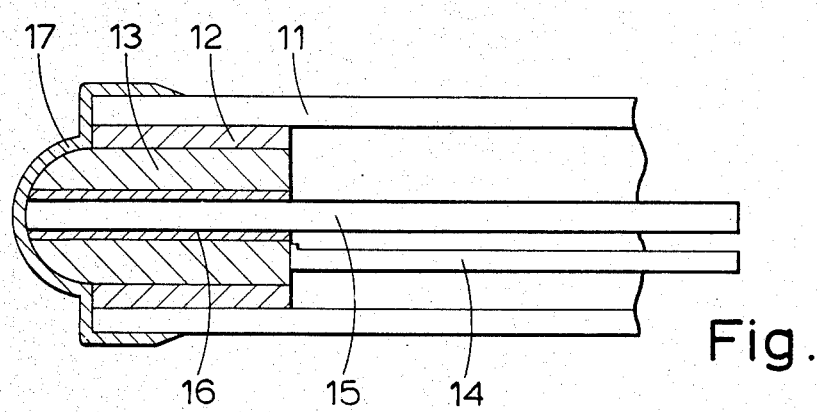
FIG. 1 shows a longitudinal section of part of a catheter tip mounted electrochemical sensor suitable for measuring the concentration of oxygen dissolved in blood.

The electrode of FIG. 1 has a catheter (11) and a pellet (13) bonded into one end by suitable material such as an epoxy adhesive (12). The pellet has a tapered nose. A connecting wire (14) is attached to the pellet through the catheter (11). The pallet has a central hole through which passes centrally a silver wire (15). The silver wire (15) passes through the catheter (11) and is secured in the hole in the pellet by suitable material such as an epoxy resin (16). The end of the wire is flush with the free end of the pellet. The layer of hydrophilic polyurethane (17) covers the pellet (13) completely and extends onto the catheter (11).

Figure 2:
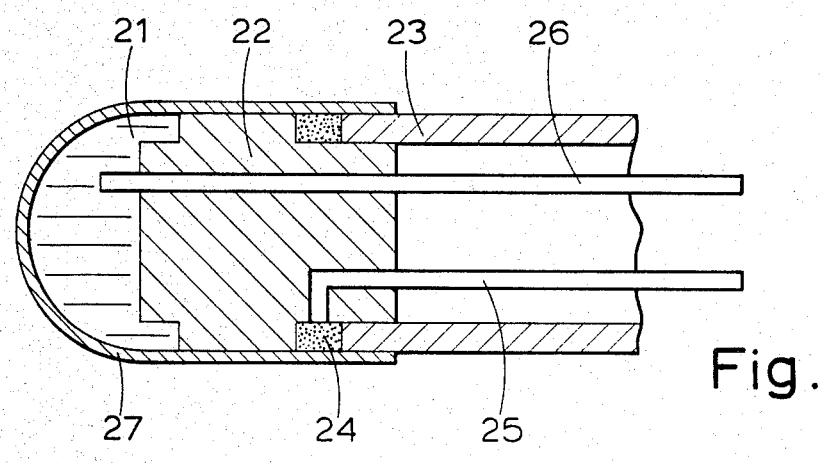
FIG. 2 shows a longitudinal section of part of a catheter tip mounted electrochemical sensor suitable for measuring the concentration of carbon dioxide dissolved in blood.

The electrode of FIG. 2 has a carbon dioxide sensor which has a solid sensing electrode (21) bonded to an epoxy resin insulator (22). The insulator (22) is bonded to a catheter (of for example PVC or nylon) (23) in such a way that an annular silver reference electrode (24) is retained as shown. The sensing electrode (21), the insulator (22), the reference electrode (24) and the catheter (23) form a smooth cylinder of diameter 1.5 mm with a hemispherical end. Electrical conductors (25) and (26) connect the reference electrode and sensing electrode to a conventional meter. The sensing electrode (21) is a palladium-hydrogen electrode. The silver reference electrode (24) of the sensor is coated with silver chloride. The sensor is coated with an electrolyte coating by dipping it into a 1.0 molar solution of sodium chloride and 0.01 molar sodium bicarbonate and allowing it to dry. A continuous coating of hydrophilic polyurethane (27) is formed over the sensor by dipping it in a 4% solution of the polymer in a 50/50 mixture of methylene chloride and ethanol. The coating (27) covers the sensing electrode (21), the silver reference electrode (24) and extend onto the catheter (23). The coating produced is about 20 microns thick.

Figure 3:
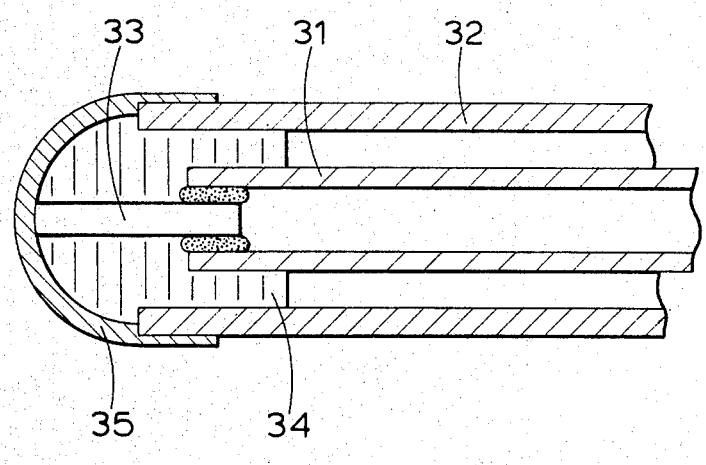
FIG. 3 shows a longitudinal section of a monopolar oxygen sensor mounted in the tip of a catheter.

In the electrode of FIG. 3 a hollow electrical conductor (31) such as a stainless steel tube is enclosed in PVC (32) to provide an insulating physiologically inert coating. An electrode (33) such as a gold wire is enclosed in an electrically insulating material (34) such as an epoxy resin to form the tip of the probe. The whole tip of the electrode is coated in a layer of hydrophilic polyurethane (35) by dip coating from a 4% solution of the hydrophilic polymer in 50/50 mixture of methylene chloride and ethanol containing 2% water. The resulting coat was approximately 20 micron thick. (a coat approximately 40 micron thick can be obtained from a 5% solution). The stainless steel tube provides support for the electrode and a means of connecting the electrode to a suitable measuring instrument. The probe is used in conjunction with a reference electrode in conventional manner.

Figure 4:
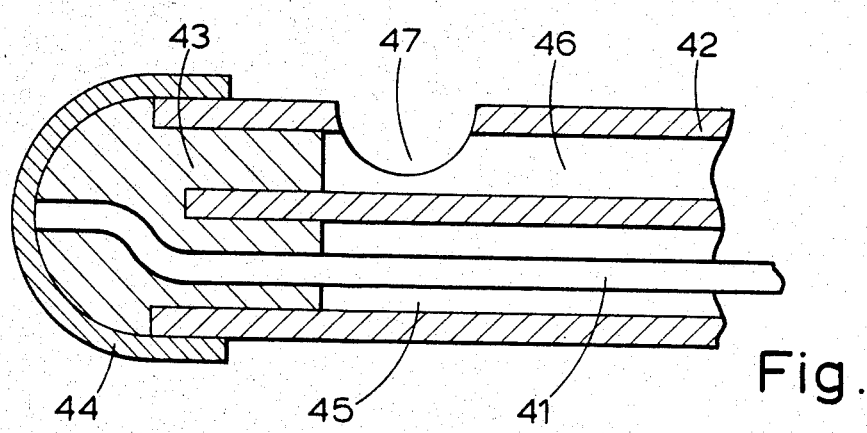
FIG. 4 shows a longitudinal section of a monopolar sensor mounted in the tip of a bilumen catheter.

The electrode of FIG. 4 is a monopolar bilumen catheter electrode for measuring dissolved oxygen in blood which are formed by mounting a silver wire (41) of diameter 100 micron in a PVC catheter (42) using an epoxy resin plug (43) to locate the wire and seal the end of the catheter. The electrode, epoxy plug and the end of the catheter are coated with an approximately 18 micron thck layer of hydrophilic polyurethane (44) by dip coating from a 3.8% solution of hydrophilic polyurethane in 50/50 methylene chloride and ethanol containing 2% water. In use the catheter is inserted intravenously, for example umbilically into a neonate. A reference electrode will be also connected in conventional manner. In this catheter one lumen (45) is used to carry the oxygen sensing electrode. The second lumen (46) may be used to withdraw blood samples for analysis. The second lumen (46) is provided with access through the port which may be in the wall of the catheter (47) or at the onward facing tip of the catheter.

Figure 5:
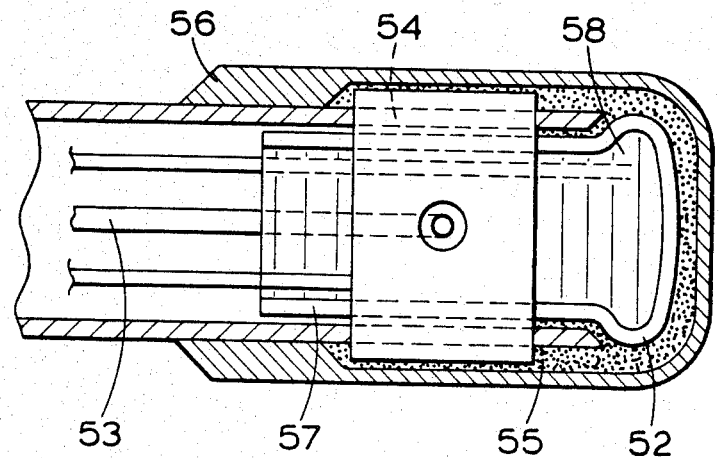
FIG. 5 shows a longitudinal section of a bifunctional sensor adapted to measure the partial pressures of oxygen and carbon dioxide dissolved in the blood which sensor is mounted in the tip of a catheter.

The electrode of FIG. 5 is an electrochemical sensor which is mounted in the tip of a PVC catheter (51). The electrochemical sensor has a carbon dioxide sensitive electrode (52) in the form of a pH glass head mounted in the end of the catheter and an oxygen electrode which is a 180 micron diameter silver wire (53). Electrodes (52) and (53) are common to a Ag/AgCl reference electrode (54). The area of the catheter carrying the electrode is covered with a layer of alkaline electrolyte (55) consisting of a semi-solid sodium bicarbonate, potassium chloride electrolyte. The sensor is coated in an approximately 25 micron thick hydrophilic polyurethane membrane (56) by dip coating from a 4.25% solution in 50/50 methylene chloride and ethanol containing 2% water. The pH glass electrode (52) is mounted on a hollow lead glass shaft (57) closed by a silicone rubber seal (not shown). The lumen of the glass shaft is fitted with a chloride ion gelled electrolyte or alternatively an electrically conductive epoxy resin (58). The carbon dioxide electrode (52) and the oxygen electrode (53) are 2-4 mm apart.

Figure 6:
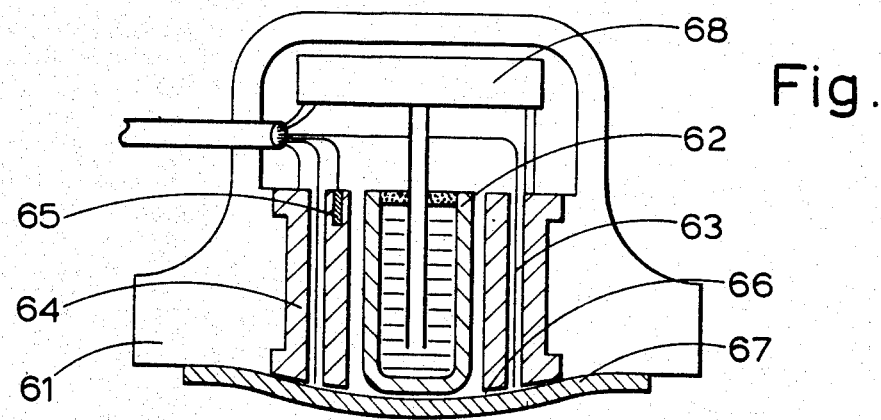
FIG. 6 shows a cross section of a bifunctional sensor for transcutaneous measurement of oxygen and carbon dioxide dissolved in the blood.

The electrode of FIG. 6 is a transcutaneous electrode in which a sensor body (61) has positioned therein a centrally arranged pH glass electrode (62) for measuring carbon dioxide. Surrounding the pH electrode is an annular silver/silver chloride reference anode (64) and positioned therein and insulated therefrom are two radially opposed platinum oxygen electrodes (63). The reference anode (64) is provided with a heater the temperature of which is controlled by a thermistor (65) positioned in the reference electrode. The exposed surfaces of the electrodes are coated with an electrolyte mixture (66) of $NaHCO_3$ and KCl by dipping in a 0.4 l molar solution of $NaHCO_3$ and 1 molar KCl. After drying the electrolyte layer is coated with a 10 micron thick membrane of hydrophilic polyurethane (67) by dip coating from a 2% solution in 50/50 methylene chloride and ethanol containing 2% water. The layer of hydrophilic polyurethane covers the exposed electrode surface and extends onto the sensor body (61). A field effect transistor (68) is provided to lower the impedance of the $CO_2$ electrode. In use the sensor is placed in contact with the skin of the patient and the heater is activated to raise the temperature of the skin to a value sufficient to increase blood flow locally.

Figure 7:
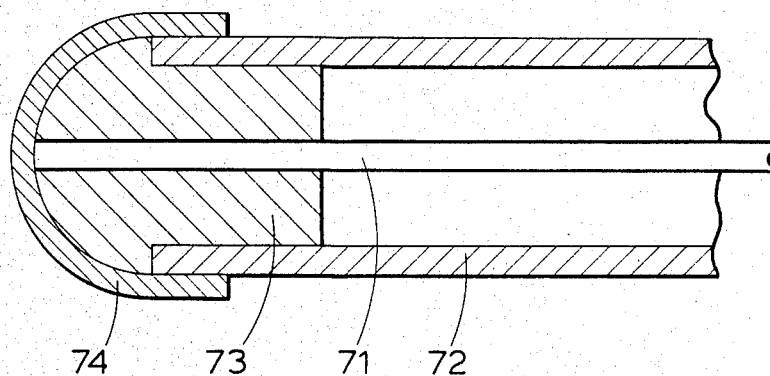
FIG. 7 shows a longitudinal section of a monopolar oxygen sensor of particularly simple construction mounted in the tip of a catheter.

The electrode of FIG. 7 is a monopolar catheter electrode of simple construction for measuring dissolved oxygen in blood and is formed by mounting a silver wire (71) of diameter 100 micron in a PVC catheter (72) using an epoxy resin plug (73) to locate the wire and seal the end of the catheter. The electrode, epoxy plug and then end of the catheter are coated with an approximately 25 micron thick layer of hydrophilic polyurethane (74) by dip coating from a 4.2% solution of hydrophilic polyurethane in 50/50 methylene chloride and ethanol containing 2% water. The catheter is normally employed intravenously, for example umbilically into a neonate.

Figure 8:
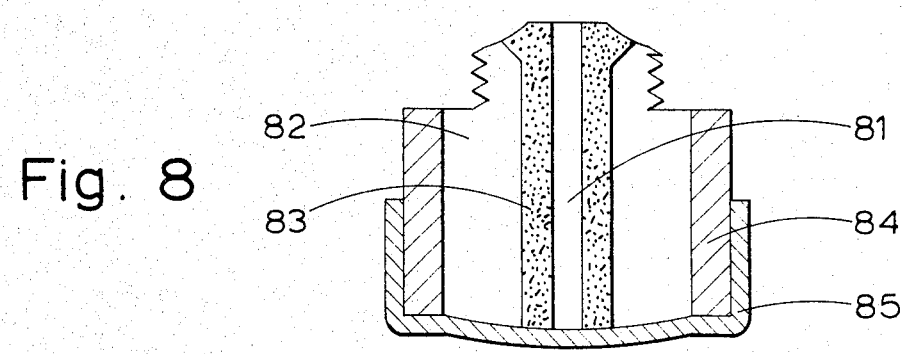
FIG. 8 shows a section of a disposable skincontact oxygen electrode assembly suitable for use with a cooperating reusable base.

The electrode of FIG. 8 has a central cathode (81) insulated from a surrounding catheter (82) by a glass insulator (83). The catheter is itself surrounded by a cover (84). The preceeding parts may be bound in place by an epoxy resin. The body contacting face and part of the cover is coated with a hydrophilic polyurethane membrane (85). The electrode may be activated by wetting with electrolyte solution in conventional manner.

Figure 9:
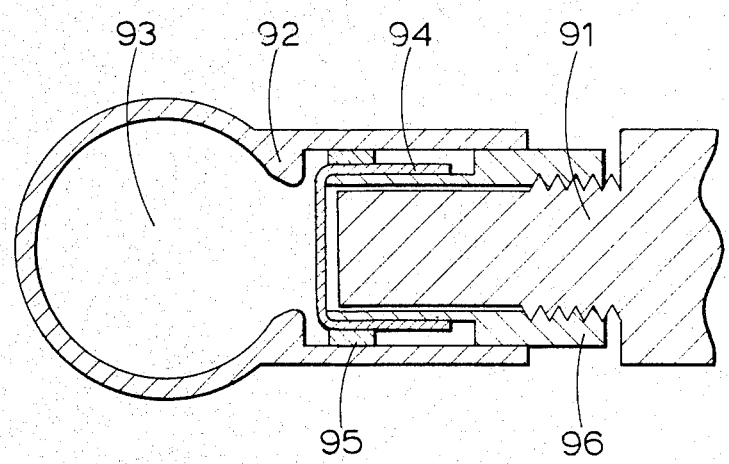
FIG. 9 shows a section of an oxygen electrode and its co-operating assembly for use with an extracorporeal circulation of blood.

The electrode of FIG. 9 consists of an oxygen sensing electrode assembly having a permanent part (91) (not shown in detail) and a disposable portion consisting of a housing (92) having a flow chamber (93) for the blood to be monitored, a membrane (94) retained by a ring (95) and a mounting member (96) by which the disposable portion is attached to the permanent body of the electrode (91). The membrane (94) is a cast film of hydrophilic polyurethane of thickness 25 micron. An alternative membrane may be a 10 micron film of hydrophilic polyurethane supported by a 10 micron film of low density polyethylene.

EXAMPLE 1

General Preparative Procedure

The required quantities of polyglycol, chain extenders (aliphatic diol or diamine) and water were warmed to approximately 80° C. and mixed completely in a covered beaker. The required quantity of di-isocyanate was added to the warm mixture and the total mass stirred until a clear solution resulted. The temperature was allowed to fall to 70° C. at which point the appropriate weight of catalyst was added from a syringe and the mixture stirred continuously until exothermic reaction reached 90° C. when it was poured quickly into a polypropylene tray and transferred immediately to an oven to cure for ½ hour at 100° C. The resulting foam was left at room temperature for at least 16 hours before cutting into pieces. (These pieces could be dissolved in a convenient solvent such as dichloromethane, methanol or mixtures thereof to form a solution suitable for coating objects).

Hydrophilic polyurethanes were prepared by the above procedure using polyethylene glycol 1540 (supplied by Union Carbide Corp.), polytetramethylene glycol 1010 (supplied by Quaker Oats Corporation) ethane diol and 4,4'dicyclohexylmethane di-isocyanate (supplied as Hylene W by Du Pont or Desmodur W by Bayer).

The materials also include 0.25% water and 0.2% di-n-butyltinlaurate solution (Catalyst T-12).

| Mole ratio of polyglycol to ethandiol | Mole % polyethylene glycol 1540 to Polymeg | % Water |
| --- | --- | --- |
| 1:0.5 | 5.0 | 10 |
| " | 10.0 | 16 |
| " | 20.0 | 16 |
| 1:1 | 5.0 | 8 |
| " | 10.0* | 11 |
| " | 12.5 | 15 |
| " | 15.0 | 18 |
| " | 15.0 | 17 |
| " | 17.5 | 23 |
| " | 20.0 | 30 |
| 1:1.5 | 7.6 | 9 |
| " | 10.0 | 13 |
| " | 14.0 | 19 |
| " | 17.0 | 20 |
| " | 20.0 | 26 |

*Formulation for this material is as follows:
  Material
  Polyethylene glycol 1540    9.15 g
  Polymeg 1010               53.75 g
  Ethane diol                 3.68 g
  Water                       0.05 g
  Hylene W                   33.37 g
  Catalyst T-12               0.20 ml.

Other hydrophilic polyurethanes were prepared from the following:

| Polyethylene glycol molecular weight | mole ratio of polyethylene glycol to Digol | % Water |
| --- | --- | --- |
| 600 | 1:1.13 | 21 |
| 1000 | 1:1.13 | 34 |
| *1540 | 1:1.13 | 40 |
| 6000 | 1:1.13 | 48 |

*Formulation for this material is as follows:
  Material
  Polyethylene glycol 1540   42.49 g
  Digol                       5.07 g
  Water                       0.23 g
  Hylene W                   29.50 g
  Catalyst T-12               0.2 mls.

| Polyethylene glycol molecular weight | Mole ratio of polyethylene glycol to Digol | % Water |
| --- | --- | --- |
| 1000 | 1:0.33 | 38 |
| *4000 | 1:4.77 | 39 |
| 6000 | 1:7.75 | 44 |

*Formulation for this material is as follows:
  Material
  Polyethylene glycol 4000   62.59 g
  Digol                       7.91 g
  Water                       0.10 g
  Hylene W                   32.10 g
  Catalyst T-12               0.2 mls.

| mole ratio of polyglycol to 1:2 diaminoethane | Mole ratio of polyethylene glycol to polymeg 1010 | % water |
| --- | --- | --- |
| 1:1 | 1:19 | 6 |
| *1:1 | 1:9 | 12 |
| 1:1 | 1:4 | 22 |

*Formulation for this material is as follows:
  Material
  Polyethylene glycol 1540    9.16 g
  Polymeg 1010               53.81 g
  1:2 Diaminoethane           3.55 g
  Water                       0.07 g
  Hylene W                   33.41 g
  Catalyst T-12               0.2 mls.

(Amine extended polymer made by reacting isocyanate and polyglycol followed by reaction with amine).

EXAMPLE 2

A mixture of the following:

Polyethylene glycol 1540   15.4 g     (0.01 mole)
  Polypropylene glycol 1025  30.75 g    (0.03 mole)
  Ethane diol                 3.71 g    (0.06 mole)
  Di-n-butyl tin di-laurate   0.15 g was heated in a beaker to 50° C. on a hot plate with constant stirring. Hylene W (27.5 g; 0.11 moles) was added to the mixture which was stirred to 30 seconds when it became clear. The mixture was immediately poured into a mold (high density polythene) and placed in an oven at 70° C. for 1 hour. After removal from the oven the resulting hydrophilic polyurethane was left for at least 24 hours before use. (The material had a water uptake of about 26%).

EXAMPLE 3

The polymer of Example 2 may be used in place of the polystyrene membrane in the sensor specifically described in British Patent Specification No. 2 005 418 A.

EXAMPLE 4

Preparation of Hydrophilic Polyurethane on a 1 Kilogram Scale

Polyethylene glycol 1500 (193.9 g, 0.14 moles), polypropylene glycol 1025 (430.5 g, 0.42 moles) ethanediol (52.08 g, 0.84 moles) and catalyst T-12 (2.2 g) were weighed into a two liter glass beaker and placed into a fan assisted oven set at a temperature of 60° C. to melt the polyethylene glycol. When the polyethylene glycol had melted, the mixture was stirred well and Desmodur W (31.16 g, 1.6618 moles) added with continued stirring. The stirring was continued until the polymerisation mixture had changed from an opaque liquid to a clear liquid. At this point the polymerisation mixture was poured into a polypropylene mould and placed in a fan assisted oven set at a temperature of 90° C. for one hour to cure. The elastomer obtained was allowed to cure for a further 24 hours at room temperature before use. The material has a water content after hydration of about 23%.

(This Example uses a little more isocyanate than in Example 2 owing to the slightly wetter diols).

EXAMPLE 5

Dip Coating

A polargraphic bipolar silver, silver/silver chloride oxygen electrode mounted in the distal end of a 1.5 mm medical grade transparent polyvinyl chloride catheter was dip coated with the dry hydrophilic polyurethane of Example 3 as follows:

Into a solution of the hydrophilic polyurethane in 1:1 methylene chloride and ethanol containing 2% water was dipped the first 1 cm of the catheter carrying the electrode. The cathether was kept in the solution for about 5 seconds and then withdrawn vertically upward and maintained in this configuration in air for 1 minute and then in an oven at 70° C. for a further five minutes. In some cases the whole process was repeated. The resulting membranes had the following thicknesses:

| Concentration (%) | No. of Dips | Coating Thickness (Micron) |
| --- | --- | --- |
| 2 | 1 | 3.6 |
| 3.5 | 1 | 10 |

-continued

| Concentration (%) | No. of Dips | Coating Thickness (Micron) |
| --- | --- | --- |
| 5 | 1 | 35 |
| 6.5 | 1 | 62 |
| 8.74 | 1 | 136 |
| 2 | 2 | 8.3 |
| 3.5 | 2 | 16.4 |
| 5 | 2 | 22.9 |

What we claim is:

1. In an electrochemical sensor for use in determining blood gas which employs a membrane of material permeable to the blood gas to be determined, the improvement which comprises employing as the membrane a membrane which consists essentially of a hydrophilic linear polyether polyurethane.

2. The improvement according to claim 1 wherein the electrochemical sensor includes a body contacting surface and the membrane of hydrophilic linear polyether polyurethane is coated on the body contacting surface of said sensor.

3. The improvement according to claim 1 wherein the electrochemical sensor includes a surface for contact with arterial or venous blood and the membrane of hydrophilic linear polyether polyurethane is coated on the blood contacting surface of said sensor.

4. The improvement according to claim 1 wherein the hydrophilic linear polyether polyurethane contains 10 to 40% water when hydrated.

5. The improvement according to claim 4 wherein the hydrophilic linear polyether polyurethane contains 20 to 30% water when hydrated.

6. The improvement according to claim 1 wherein the membrane is emplaced in a non-hydrated form by dip coating from a non-aqueous solution of the hydrophilic linear polyether polyurethane.

7. The improvement according to claim 1 wherein the membrane is from 10 to 25 microns thick.

8. In a catheter having an oxygen electrode including a membrane which electrode is operatively mounted at the distal end of the catheter for intravenous use and which electrode employs a membrane permeable to oxygen, the improvement which comprises employing a membrane which consists essentially of a hydrophilic linear polyether polyurethane which when hydrated contains 10 to 40% water as the membrane.

9. The improvement according to either of claims 1 or 8 wherein the hydrophilic linear polyether polyurethane has the ether units containing poly(ethylene glycol) derivable blocks and poly (prop- or but-)ylene glycol derivable blocks in the mole ratio of 1:2 to 1:10 and ethane diol wherein the mole ratio of ethane diol to polyglycol derivable blocks is from 5:2 to 1:3.

10. In an oxygen electrode for monitoring oxygen levels which includes a protective membrane which is permeable to oxygen, the improvement which comprises employing as the protective membrane, a membrane which consists essentially of a hydrophilic linear polyether polyurethane.

* * * * *